United States Patent
Dhanantwari et al.

(10) Patent No.: US 10,706,506 B2
(45) Date of Patent: Jul. 7, 2020

(54) IMAGE QUALITY INDEX AND/OR IMAGING PARAMETER RECOMMENDATION BASED THEREON

(71) Applicant: KONINKLIJKE PHILIPS N.V., Eindhoven (NL)

(72) Inventors: Amar Dhanantwari, Solon, OH (US); Dhruv Mehta, South Euclid, OH (US); Yael Nae, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 658 days.

(21) Appl. No.: 14/782,727

(22) PCT Filed: Apr. 3, 2014

(86) PCT No.: PCT/IB2014/060401
§ 371 (c)(1),
(2) Date: Oct. 6, 2015

(87) PCT Pub. No.: WO2014/167463
PCT Pub. Date: Oct. 16, 2014

(65) Prior Publication Data
US 2016/0042499 A1 Feb. 11, 2016

Related U.S. Application Data

(60) Provisional application No. 61/810,417, filed on Apr. 10, 2013.

(51) Int. Cl.
*G06T 5/00* (2006.01)
*G06T 11/00* (2006.01)
*A61B 6/00* (2006.01)

(52) U.S. Cl.
CPC ............ *G06T 5/002* (2013.01); *A61B 6/5258* (2013.01); *G06T 11/003* (2013.01); *G06T 11/005* (2013.01); *G06T 2207/10081* (2013.01)

(58) Field of Classification Search
None
See application file for complete search history.

(56) References Cited

U.S. PATENT DOCUMENTS 7,088,849 B1   8/2006   Toth
7,756,312 B2   7/2010   Hsieh et al.
(Continued)

FOREIGN PATENT DOCUMENTS

DE   102008052691 A1   4/2010
EP   0981998 A1   3/2000
(Continued)

OTHER PUBLICATIONS

Belanger, B., et al.; Management of pediatric radiation dose using GE fluoroscopic equipment; 2006; Pediatric Radiology; 36(2)204-211.

*Primary Examiner* — Jiangeng Sun
(74) *Attorney, Agent, or Firm* — Larry Liberchuk

(57) ABSTRACT

A method includes determining a low contrast detectability of a scan and generating an image quality index based on the determined low contrast detectability. Another method includes identifying an image quality index of interest, identifying an acquisition and/or reconstruction parameter based on the image quality index and a pre-determined mapping between image quality indexes and acquisition parameter and reconstruction parameters, and displaying the identified acquisition and/or the reconstruction parameter. A system (100) includes a metric determiner (122) that determines a first image quality index for a scan based on at least one of a low contrast detectability of the scan or a project domain noise of the scan, and/or a parameter recommender (126) that recommends at least one of an acquisition or a reconstruction parameter for a scan based on a second image (Continued)

quality index, and a display (114) that visually presents the first or second image quality index.

17 Claims, 5 Drawing Sheets

(56) References Cited

U.S. PATENT DOCUMENTS

| | | |
|---|---|---|
| 2007/0014480 A1 | 1/2007 | Sirohey et al. |
| 2007/0053477 A1* | 3/2007 | Ning .................. G01N 23/046 378/4 |
| 2008/0159643 A1 | 7/2008 | Huang et al. |
| 2009/0256565 A1 | 10/2009 | Marinelli et al. |
| 2010/0097378 A1 | 4/2010 | Barth et al. |
| 2011/0052030 A1 | 3/2011 | Bruder et al. |
| 2011/0257919 A1* | 10/2011 | Reiner ................ G06F 17/3028 702/81 |
| 2011/0282181 A1 | 11/2011 | Wang et al. |
| 2011/0286629 A1 | 11/2011 | Dennerlein |
| 2012/0018645 A1 | 1/2012 | Vija |
| 2012/0106817 A1* | 5/2012 | Shih ...................... A61B 6/583 382/131 |
| 2012/0230576 A1* | 9/2012 | Rohler ................ A61B 6/032 382/132 |
| 2013/0116554 A1* | 5/2013 | Kaiser ................ A61K 49/0438 600/425 |
| 2014/0270454 A1* | 9/2014 | Chen ...................... G06T 5/002 382/132 |

FOREIGN PATENT DOCUMENTS

| | | |
|---|---|---|
| EP | 2385494 A1 | 11/2011 |
| WO | 0007146 A1 | 2/2000 |
| WO | 2007034342 A2 | 3/2007 |
| WO | 2008146186 A2 | 12/2008 |
| WO | 2009083864 A2 | 7/2009 |
| WO | 2009091824 A1 | 7/2009 |
| WO | 2009129137 A1 | 10/2009 |
| WO | 2010082101 A1 | 7/2010 |
| WO | 2011008296 A1 | 1/2011 |
| WO | 2011036624 A1 | 3/2011 |
| WO | 2011046425 A2 | 4/2011 |
| WO | 2012131520 A2 | 10/2012 |
| WO | 2013049818 A1 | 4/2013 |

* cited by examiner

IMAGE QUALITY INDEX AND/OR IMAGING PARAMETER RECOMMENDATION BASED THEREON

CROSS REFERENCE TO RELATED APPLICATIONS

This application is a national filing of PCT application Serial No. PCT/IB2014/060401, filed Apr. 3, 2014, published as WO 2014/167463 A2 on Oct. 16, 2014, which claims the benefit of U.S. provisional application Ser. No. 61/810,417 filed Apr. 10, 2013, which is incorporated herein by reference.

The following generally relates to imaging and is described with particular application to computed tomography (CT). However, the following is also amenable to other modalities.

In CT imaging, the choices of acquisition and/or reconstruction parameters can be very specific to the imaging task at hand. For example, one scan may be for low contrast tissue such as a liver tumor, while another scan may be for bone, which is high contrast tissue. This means that the radiologist and/or technologist need to translate between the clinical indication (i.e., the reason) and the parameters. However, variability of training of imaging staff could lead to variability in parameter selection and hence diagnostic quality of the images. In addition, individual radiologists may have different preferences that vary for a given type of study.

Furthermore, with non-traditional reconstruction algorithms such as de-noising reconstruction algorithms, the traditional imaging trade-offs may no longer apply. For example, when traditional image reconstruction algorithms are used in CT imaging, the noise in the resulting image is usually a good indicator of the quality of the image. In many cases, the image noise is the only indicator used to represent image quality, e.g., dose modulation algorithms target uniform image noise in the image volume as a way to achieve constant image quality. However, with some or all of the noise removed from an image, the reader no longer has the visual noise cues that indicate the quality of the image or a level of confidence that should be placed in the image.

Furthermore, traditional image quality metrics tend to consider the noise in the final image and/or image spatial resolution. Such metrics may provide misleading information when used with de-noising reconstruction algorithms as two image data sets acquired with different dose levels may result in images with similar image noise even though they correspond to different quality acquisitions, e.g., a decrease in dose may result in a significant change in low contrast detectability. Moreover, metrics based on spatial resolution tend to emphasize high contrast targets, such as bone, which, generally are not susceptible to dose reduction.

Aspects described herein address the above-referenced problems and others.

The following describes an approach in which a clinical indication and/or a low contrast detectability (i.e., the ability to detect low contrast objects) is utilized to identify at least one of an acquisition or reconstruction parameter and/or compute an index indicative of a quality of an acquisition (e.g., dose) and/or a confidence in an ability to detect low contrast objects in the resulting image data.

In one aspect, a method includes determining a low contrast detectability of a scan and generating an image quality index based on the determined low contrast detectability.

In another aspect, a method includes identifying an image quality index of interest, identifying a set of acquisition and/or reconstruction parameters based on the image quality index, the object being scanned, and a pre-determined mapping between image quality indexes and acquisition parameter and reconstruction parameters, and displaying the identified acquisition and/or the reconstruction parameter.

In another aspect, a system includes a metric determiner that determines a first image quality index for a scan based at least one of a low contrast detectability of the scan or a project domain noise of the scan, and/or a parameter recommender that recommends at least one of an acquisition or a reconstruction parameters for a scan based on a second image quality index, and a display that visually presents the first or second image quality index.

The invention may take form in various components and arrangements of components, and in various steps and arrangements of steps. The drawings are only for purposes of illustrating the preferred embodiments and are not to be construed as limiting the invention.

FIG. 1 schematically illustrates an imaging system in connection with a metric determiner and a parameter recommender.

As described in greater detail below, a clinical indication and/or a low contrast detectability is utilized to identify at least one of an acquisition or reconstruction parameter and/or compute an index indicative of quality of an acquisition and/or a confidence in an ability to detect low contrast objects in the resulting image data. This approach is well-suited for de-noising reconstruction algorithms because the image quality index provides information about the visable noise removed by the reconstruction.

Figure 1:
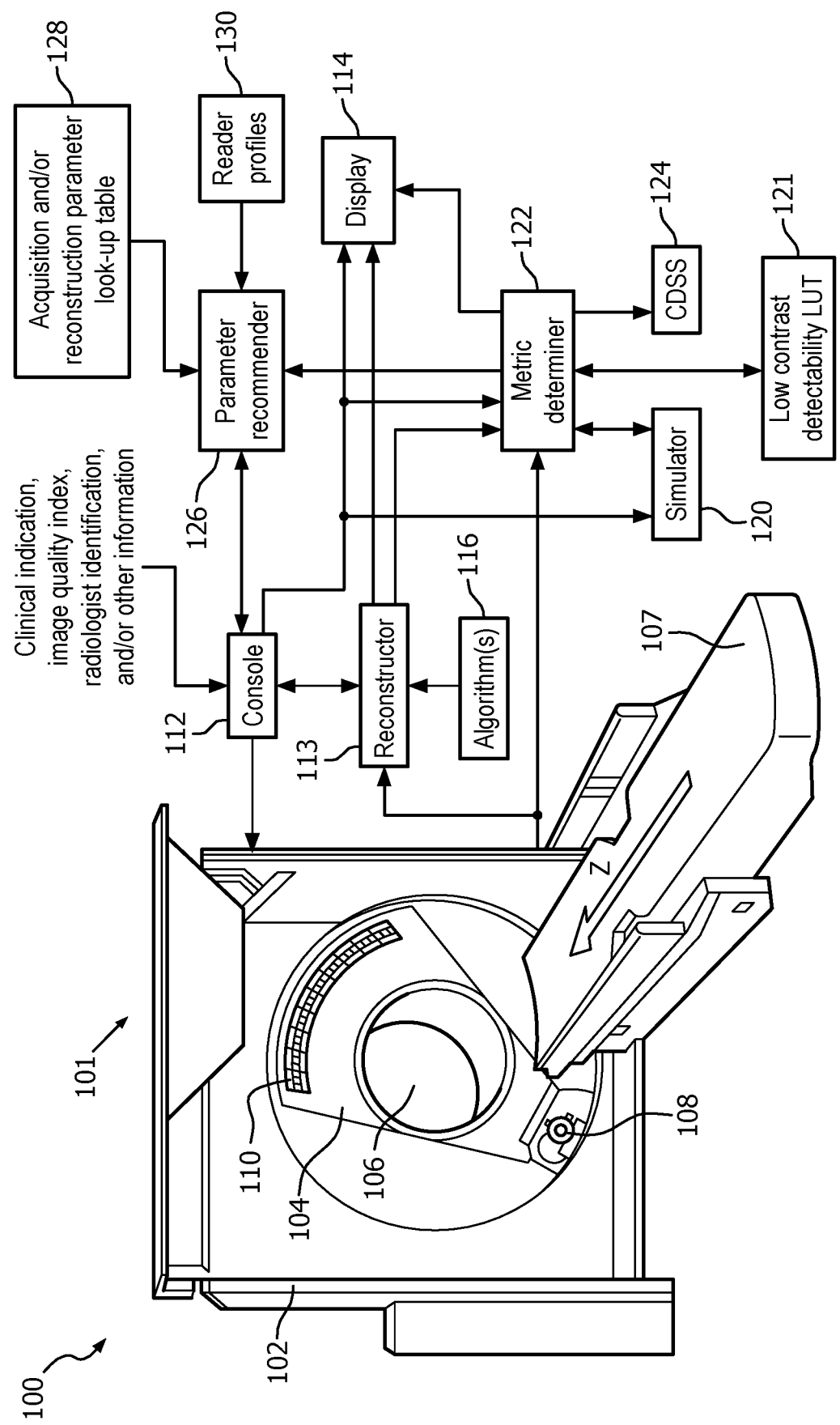

FIG. 1 illustrates a system 100 including an imaging apparatus 101 such as a computed tomography (CT) scanner. The imaging apparatus 101 includes a generally stationary gantry 102 and a rotating gantry 104. The rotating gantry 104 is rotatably supported by the stationary gantry 102 and rotates around an examination region about a longitudinal or z-axis. A patient support 106, such as a couch, supports an object or subject such as a human patient in the examination region.

A radiation source 108, such as an x-ray tube, is rotatably supported by the rotating gantry 104. The radiation source 108 rotates with the rotating gantry 104 and emits radiation that traverses the examination region. A radiation sensitive detector array 110 subtends an angular arc opposite the radiation source 108 across the examination region. The detector array 110 includes rows of detectors that extend along the z-axis direction, detect radiation traversing the examination region, and generates projection data.

A general-purpose computing system or computer serves as an operator console 112 and includes an input device(s) such as a mouse, a keyboard, and/or the like and an output device(s) such as a display monitor 114, a filmer or the like. The console 112 allows an operator to interact with and/or control operation of the system 100. This includes providing information such as a clinical indication, an image quality index of interest, a reading radiologist identification, and/or other information.

A reconstructor 113 reconstructs the projection data, generating volumetric image data indicative of a scanned portion of a subject or object located in the imaging region 106. The reconstructor 113 can employ various reconstruction algorithms 116, including, but not limited to, filtered-backprojection (FBP), iterative, and/or other reconstruction algorithms. This includes employing traditional (or non-denoising) and/or de-noising, including iterative, reconstruction algorithms.

The system 100 further includes a simulator 120 with a computer processor and computer readable instructions stored on computer readable storage medium, which, when executed by the computer processor causes the processor to simulate a scan. This includes receiving acquisition and/or reconstruction parameters (e.g., entered by a user and/or accepted computer suggested parameters) and generating simulated projection data and/or image data. The simulator 120 can be part of the console 112 and/or a separate computing system.

The system 100 further includes a metric determiner 122 that determines at least one metric for a scan and/or simulated scan. In this illustrated embodiment, the metric determiner 122 determines the metric based on one or more of projection data, image data, or low contrast detectability. The projection data and/or image data can be obtained from the imaging apparatus 101 and/or the simulator 120, and/or derived from parameters entered into the console 112, and the low contrast detectability can be obtained from a look up table (LUT) 121 and/or otherwise.

Figure 2:
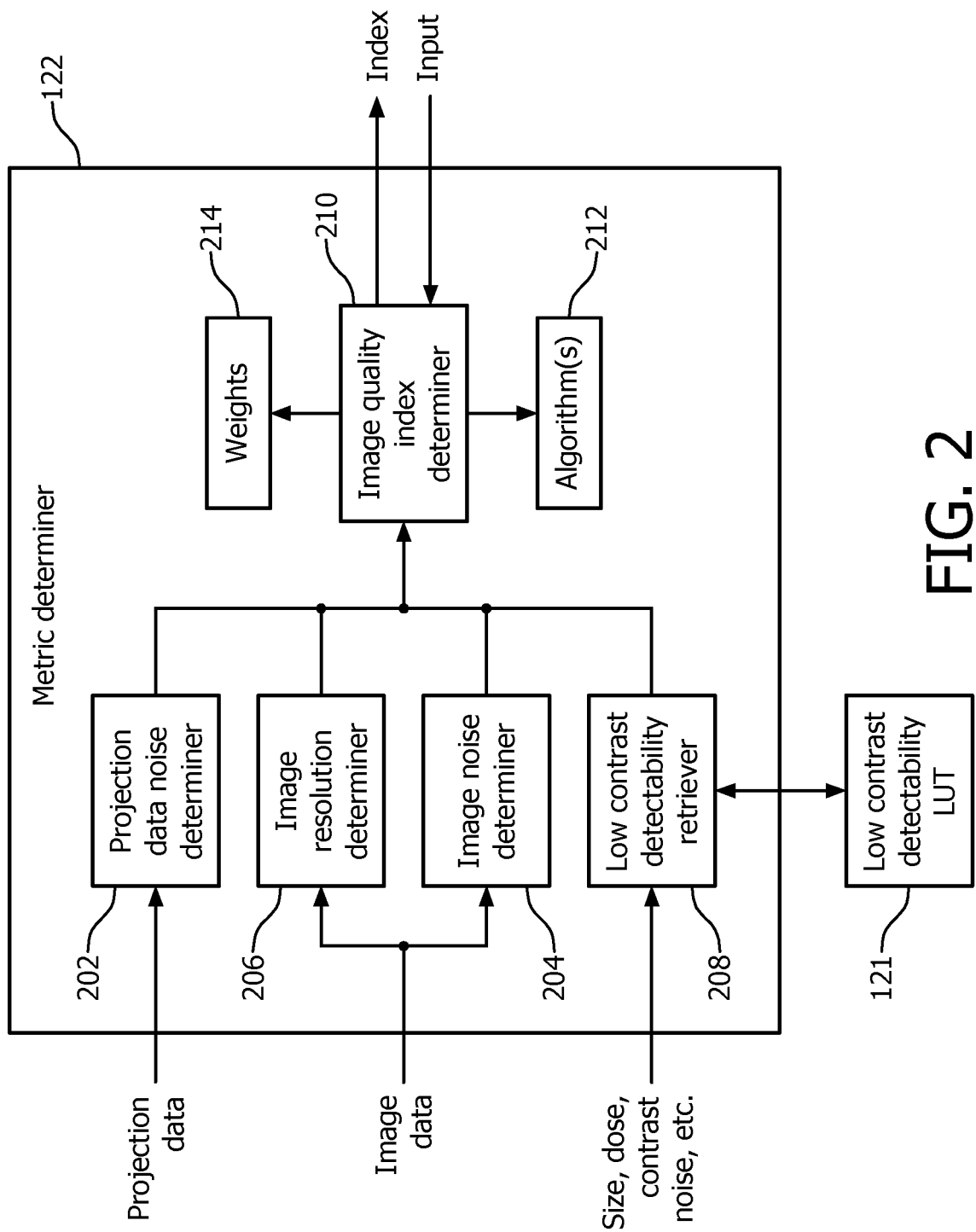
FIG. 2 illustrates a non-limiting example of the metric determiner.
Figure 3:
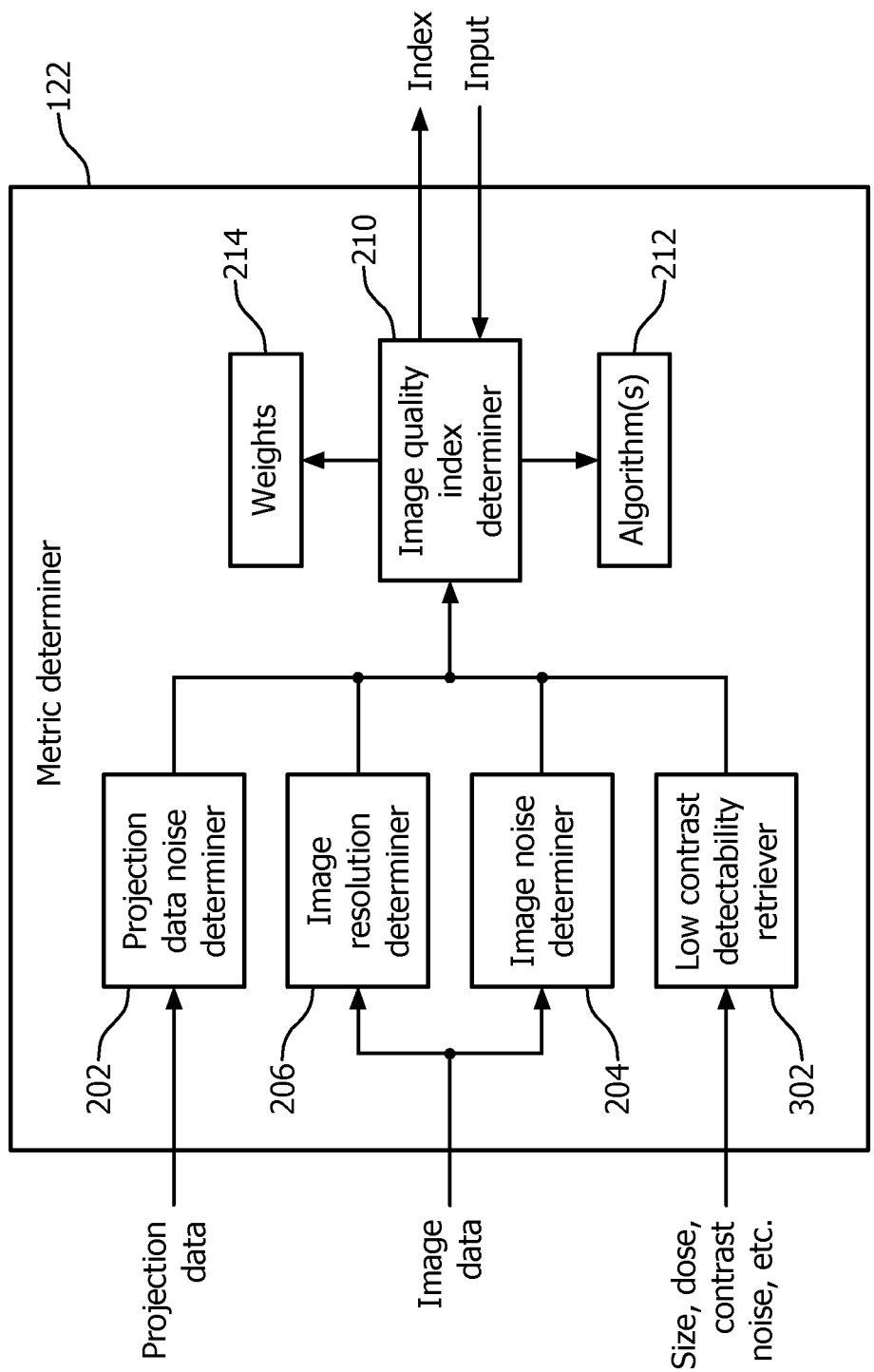
FIG. 3 illustrates another non-limiting example of the metric determiner.

FIGS. 2 and 3 illustrate non-limiting examples of the metric determiner 122.

In FIG. 2, a projection data noise determiner 202 receives, as an input, the projection data and determines projection domain noise based thereon. An image data noise determiner 204 receives, as an input, the image data and determines image domain noise based thereon. An image resolution determiner 206 also receives, as an input, the image data, but determines an image resolution based thereon. A low contrast detectability retriever 208 receives, as an input, information such as object size, object contrast, dose/noise, etc., and utilizes this information to identify a low contrast detectability from the LUT 121.

The low contrast detectability LUT 121 can be variously generated. For example, the low contrast detectability can be determined based on readings by a reader(s) observing a set of training images having a known object contrast and different levels of noise, object size, etc. Generally, increasing noise and/or decreasing object size results in a lower percentage of correct readings, which translates to a lower confidence level, while decreasing noise and/or increasing object size results in a higher percentage of correct readings, which translates to a higher confidence level.

The relationship between the reading results and the object size, noise/dose, etc. can then be used to generate the low contrast detectability LUT 121, where each combination of the factors is associated with an entry in the LUT 121, which stores a detectability or confidence level. In a variation, a computer model is generated based on the results from the readers. The computer model is then executed by a computer microprocessor to read an input set of images, with the results being used to generate the low contrast detectability LUT 121.

An image quality index determiner 210 determines an image quality index based on the output of one or more of the projection domain noise, the image domain noise, the image resolution, or the low contrast detectability using an algorithm(s) 212. In the illustrated embodiment, a set of weights 214 can be utilized to influence the impact of any one of these outputs, relative to the other outputs, in the determination. In the illustrated example, a user input can be used to identify which, if any, of the outputs should be weighted higher, the same, or lower, with respect to the other outputs.

For example, if the user is interested in a high confidence of low contrast detectability (e.g., when looking for a liver lesion), the input may indicate to weight the low contrast detectability input higher than the other input or to only use the low contrast detectability input. Likewise, if the relative dose of the scan is of interest, the input indicates that projection data noise should be higher weighted. This may be the case where two different dose levels produce images with a same noise level, for example, due to a de-noising reconstruction algorithm. This information could alternatively be user programmable.

FIG. 3 illustrates a variation of FIG. 2 in which a low contrast detectability determiner 302 determines a low contrast detectability confidence in real time, on demand or as needed, i.e., at the time the image quality index is being determined. In this variation, the low contrast detectability determiner 302 can process data for a scan being planned (e.g., object size, surview, kV, mAs.) and/or data derived therefrom (e.g., nose, dose, etc.), and/or access the training set of images discussed above.

Returning to FIG. 1, the metric determiner 122 can visually present the determined image quality index via the display 114 and/or convey to the image quality index to one or more other components. As discuses herein, the metric can provide an indication of a quality of a scan (e.g., the dose of the acquisition), even where a de-noising algorithm is utilized such that the noise visual cues are not present. Furthermore, the metric can indicate a confidence in which a reader can have in an image with respect to low contrast objects.

In one example, the image quality index is a value between one (1) and ten (10) where one (1) indicates low quality and/or low confidence, and ten (10) indicates high quality and/or high confidence. Other numerical ranges can also be utilized. Furthermore, other indicia can be utilized. For example, in another instance, the image quality index is represented through terms such as "low," "medium," and "high." Still other indicia is contemplated herein.

Generally, a particular value may have different meaning depending on the clinical indication and/or application. That is, a value of five (5) may indicate good quality and confidence for clinical indication "A" and/or application "A," but not acceptable quality and confidence for clinical indication "B" and/or application "B." For example, the application "A" may relate to segmenting bone tissue, which has a high contrasted edge, whereas application "B" may relate to determining a presence of a lesion in liver tissue where the lesion and liver tissue has similar contrast.

The image quality index can be overlaid over the displayed image and/or embedded in the image. Where the image is output on film, the image quality index can be part of the hardcopy film. With an electronic file, the image quality index can include in the file head (e.g., the DICOM header) and/or otherwise included with the file. The image quality index can also be displayed in a graphical user interface (GUI) along with acquisition and/or reconstruction parameters, and/or other information.

In the illustrated example, the image quality index is provided to a clinical decision support system (CDSS) 124, which employs computer-aided decision support to identify potential findings and/or recommend a next action(s) for a patient. For example, where the CDSS 124 indicates presences of a tumor, etc., the CDSS 124 can also indicate a confidence level of a finding based on the image quality index. By way of example, where the image quality index is high, the CDSS 124 can indicate that it has high confidence with its finding, and where the image quality index is low, the CDSS 124 can indicate that it has low confidence with its finding.

A parameter recommender 126 recommends at least one of an acquisition or a reconstruction parameter for a scan of an object. The input to the acquisition and/or reconstruction parameter determiner 128 (from the console 112 in the illustrated embodiment) includes, but is not limited to, at least one of the clinical indication, the image quality index of interest, the radiologist identification, and/or the other information. An example of a clinical indication includes liver tumor, liver bleeding, cirrhosis, and/or other clinical indication for the liver and/or other anatomical tissue and/or location of tissue of interest.

In the illustrated embodiment, the parameter recommender 126 recommends by identifying a set of pre-determined parameters from an acquisition and/or reconstruction parameter look up table 128, which maps the clinical indication and/or image quality index to acquisition and/or reconstruction parameters. Thus, if a user has a particular clinical indication in mind (e.g., liver lesion), and/or a specific confidence level in mind (e.g., high confidence as expressed via the image quality index), the user can input these parameters, which determine the acquisition and/or reconstruction parameters.

Generally, the look up table 128 could be predetermined and stored or modeled and can be modified based on subsequent scans. Where the acquisition and/or reconstruction parameter look up table 128 includes multiple entries of different combinations of acquisition and/or reconstruction parameters for a same image quality index and/or clinical indication, the parameter recommender 126 can list each of the candidate sets of parameters and/or combine one or more of the candidate set to derive an optimal set. The user can select a listed candidate, including the derived candidate, and/or another set of parameters.

Optionally, the parameter recommender 126 also has access to reader (i.e., radiologist) profiles 130. In this instance, the parameter recommender 126 can use the reader identification to locate a reader profile in the reader profiles 130 for the current reader and then utilizes this information to recommend the acquisition and/or reconstruction parameter. For example, different readers may have a different preference for the noise level in a same image. In another example, a particular reader may have a different preference of noise level based on the clinical indication.

For a follow up (e.g., in connection with therapy treatment) and/or other scan where the radiologist would like a same image quality index as a previous scan or simulated scan, the output of the metric determiner 122 for the previous scan be provided as an input to the parameter recommender 126, as shown. This may facilitate comparing tissue of interest in the multiple scans. Where an increased image quality index is desired for a subsequent scan, e.g., where the current scan quality and/or low contrast detectability is deemed too low, the output of the metric determiner 122 can be provided as a base line image quality index with a margin image quality index added thereto.

The metric determiner 122 could also provide an estimated image quality index based on parameters (e.g., size of object, dose of interest, noise of interest, etc.) input to the console 112, and this image quality index can be provided to the parameter recommender 126 to drive acquisition and/or reconstruction parameters. The input parameters can be tweaked, as discussed herein, until the image quality index is within a range of interest, with the acquisition and/or reconstruction parameters for this range utilized to perform a scan.

The user, via the console 112 interface, can accept, reject and/or change a recommended acquisition and/or reconstruction parameter. Parameters can be changed via a graphical drop down menu with predetermined parameter values, a dial, a slider, and/or other graphical control, a keyboard input, voice recognition, and/or other input. Likewise, the image quality index can be changed through such controls. In this instance, a change in the image quality index will include display of a change in any acquisition and/or reconstruction parameters.

In one instance, the user can indicate which parameters can change in response to a change in the image quality index. In this instance, only those parameters which are identified as allowed to change will change, if needed, and the other parameters will not change. In another instance, certain parameters (e.g., dose) may have limits and can only change up until a limit is reached. The output of the recommender 126 can include parameters related to kV, mAs, pitch, image resolution, image matrix size, voxel resolution, estimated output noise level, estimated deposited dose, etc.

Where the recommended acquisition parameters are estimated to result in a dose level that exceeds a threshold level, the parameter recommender 126 can present the dose along with a visual warning or message. The threshold level can be level of interest of the user or a maximum limit, which cannot be exceeded and/or require authorization to be exceeded. Authorized personnel may be able to override a warning or message given permission by appropriate authority. The dose can also be provided in absence of any warning or message.

In the illustrated embodiment, the user can employ the console 112 to initially set up a scan. The information can be processed by the metric determiner 122, which computes an image quality index based on this information. If the image quality index is deemed satisfactory, the initial setup can be used to scan an object. If not, the user can manually change parameters and rerun image quality index computation. Alternatively, the parameter recommender 126 can be used to recommend set up parameters based on an allowable image quality index.

It is to be appreciated that at least the metric determiner 122 and/or the parameter recommender 126 can be implemented by way of computer readable instructions, encoded or embedded on computer readable storage medium (i.e., physical memory and other non-transitory medium), which, when executed by a microprocessor(s), cause the processor (s) to carry out the described functions thereof. Additionally or alternatively, at least one of the computer readable instructions is carried by a signal, carrier wave and other transitory medium.

Figure 4:
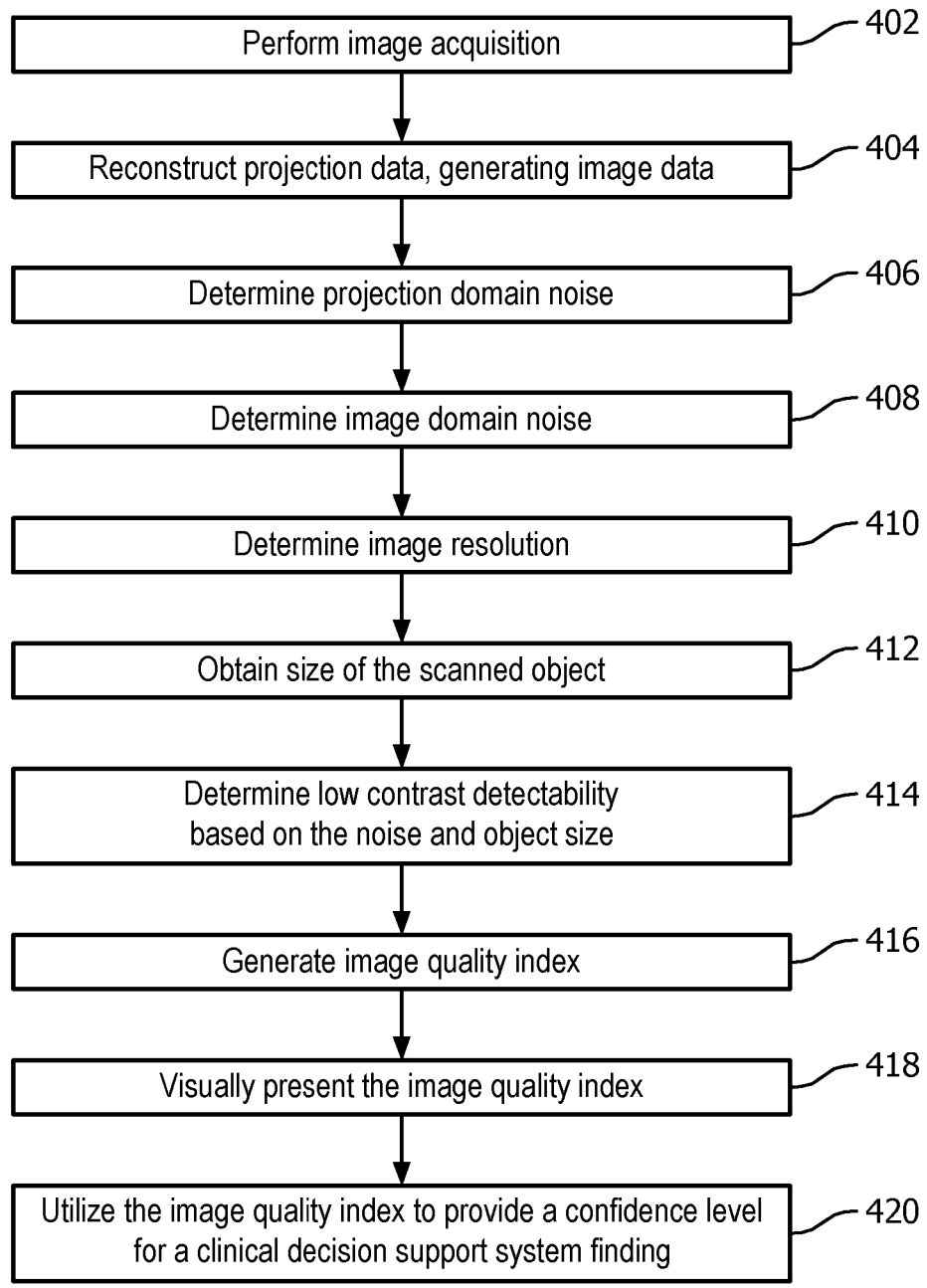
FIG. 4 illustrates an example method for determining an image quality index for an imaging acquisition.

FIG. 4 illustrates an example method for determining an image quality index for an imaging acquisition.

It is to be appreciated that the ordering of the acts is not limiting. As such, other orderings are contemplated herein. In addition, one or more acts may be omitted and/or one or more additional acts may be included.

At 402, an imaging acquisition of an object is performed, generating projection data. The scan can be an actual scan or a simulated scan.

At 404, the projection data is reconstructed, generating image data.

At 406, a projection domain noise level is determined based on the projection data.

At 408, optionally, an image domain noise level is determined based on the image data.

At 410, optionally, an image resolution is determined based on the image data.

In a variation, the projection domain noise level, the image domain noise level and/or the image resolution can be simulated and/or estimated based on the acquisition and/or reconstruction parameters for the scan.

At 412, a size of the scanned object is obtained. This can be achieved through a surview, a manual measurement provided as input, and/or otherwise.

At 414, a low contrast detectability is determined for the acquisition based on the noise level and the size and a mapping between low contrast detectability and object size and noise level. The mapping can be a pre-determined and stored manually and/or a computer generated mapping based on training data, models, etc., or generated based on the image data.

At 416, an image quality index for the acquisition is generated based on the low contrast detectability (and/or one or more of the projection domain noise level, the image domain noise level, or the image resolution).

As described herein, the image quality index indicates at least one of a quality of the acquisition (e.g., dose, noise, etc.) or a confidence in an ability to detect low contrast objects in the image data.

At 418, the image quality index is visually displayed with the image data. The image quality index can be overlaid over the image data, included in a header or other portion of an electronic file, filmed with a portion of the image data, etc.

At 420, optionally, the image data and the image quality index are provided to a clinical decision support system, which evaluates the image data, suggests a finding, and indicates a confidence level of the finding based on the image quality index.

The above acts may be implemented by way of computer readable instructions, encoded or embedded on computer readable storage medium (i.e., physical memory and other non-transitory medium), which, when executed by a microprocessor(s), cause the processor(s) to carry out the described acts. Additionally or alternatively, at least one of the computer readable instructions is carried by a signal, carrier wave and other transitory medium.

Figure 5:
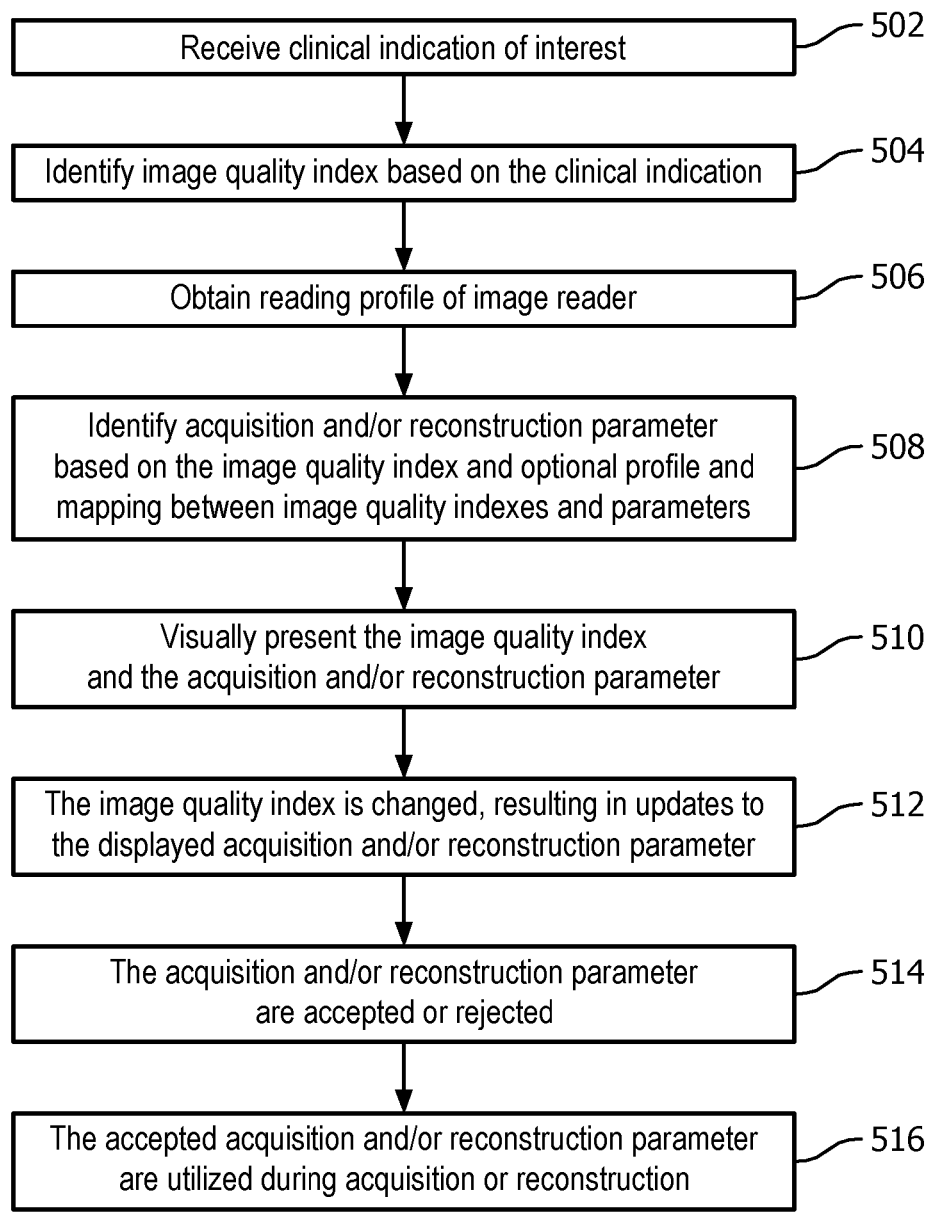
FIG. 5 illustrates an example method for utilizing an image quality index to determine an acquisition and/or reconstruction parameter.

FIG. 5 illustrates an example method for utilizing an image quality index to determine an acquisition and/or reconstruction parameter.

It is to be appreciated that the ordering of the acts is not limiting. As such, other orderings are contemplated herein. In addition, one or more acts may be omitted and/or one or more additional acts may be included.

At 502, a clinical indication of interest is received.

At 504, the clinical indication is utilized to identify an image quality index based on a mapping between clinical indications and image quality indexes.

In a variation, an image quality index of interest and not the clinical indication of interest is received.

At 506, optionally, a reading profile of a radiologist who will read the resulting image data of the acquisition is obtained. As discussed herein, the profile may contain image noise level preference and/or tolerances of the radiologist.

At 508, the image quality index (and optionally the reading profile) is utilized to identify at least one of an acquisition or reconstruction parameter based on a mapping between image quality indexes and acquisition and reconstruction parameters.

At 510, the identified image quality index and the identified acquisition and reconstruction parameters are visually presented.

At 512, optionally, the identified image quality index can be changed based on an input indicative of a user change to the image quality index, wherein the visually displayed acquisition and reconstruction parameters are updated based on the change.

At 514, the visually presented identified image quality index and the identified acquisition and reconstruction parameters are accepted or rejected.

At 516, the accepted acquisition and reconstruction parameters are employed during at least one of imaging acquisition or reconstruction.

The above acts may be implemented by way of computer readable instructions, encoded or embedded on computer readable storage medium (i.e., physical memory and other non-transitory medium), which, when executed by a microprocessor(s), cause the processor(s) to carry out the described acts. Additionally or alternatively, at least one of the computer readable instructions is carried by a signal, carrier wave and other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A computer implemented method, comprising:
   determining a low contrast detectability of a tomographic scan;
   determining projection domain noise of projection data generated from the scan;
   reconstructing image data by reconstructing the projection data using a denoising reconstruction algorithm;
   processing the image data, with a micro-processor of a clinical decision support system, which produces a result indicating a finding;
   generating an image quality index for the scan based on the determined low contrast detectability and the projection domain noise; and
   generating indicia indicating a confidence of the finding based on the image quality index.

2. The method of claim 1, further comprising:
   determining an image domain noise of the image data;
   determining an image resolution of the image data; and
   generating the image quality index based on a combination of the low contrast detectability, the projection domain noise, the image domain noise and the image resolution.

3. The method of claim 2, further comprising:
   receiving an input indicating a weighting function for the low contrast detectability, the projection domain noise, the image domain noise and the image resolution in the determination of the image quality index.

4. The method of claim 2, wherein the image quality index indicates a confidence in an ability to detect low contrast objects in the image data.

5. The method of claim 1, further comprising:
   receiving a set of candidate acquisition parameters;

determining a second image quality index for the received set of acquisition parameters; and utilizing the set of candidate acquisition parameters in response to confirming the second image quality index.

6. The method of claim 5, further comprising:

changing second image quality index, which updates the candidate acquisition parameters; and utilizing the updated set of candidate acquisition parameters.

7. The method of claim 1, wherein the image quality index indicates a quality of an acquisition of the scan.

8. The method of claim 1, wherein the image quality index indicates a patient size normalized dose of the scan.

9. A computer implemented method, comprising:

receiving a clinical indication of interest;

utilizing the received clinical indication of interest to identify an image quality index of interest based on a mapping between clinical indications and image quality indexes;

identifying at least one of an acquisition parameter or a reconstruction parameter based on the image quality index and a pre-determined mapping between image quality indexes and acquisition parameter and reconstruction parameters;

displaying the identified at least one of the acquisition parameter or the reconstruction parameter; and employing the at least one of the acquisition parameter or the reconstruction parameter to scan an object or reconstruct an image of the object with a computed tomography scanner.

10. The method of claim 9, wherein the image quality index represents at least one of a low contrast detectability or a projection domain noise.

11. The method of claim 10, wherein the image quality index further represents at least one of an image domain noise or an image resolution.

12. The method of claim 9, wherein the clinical indication of interest includes one of a liver tumor, a liver bleeding, or cirrhosis.

13. The method of claim 9, further comprising:

obtaining an image reader profile, which indicates a clinician's preference or tolerance for noise in an image; and identifying the at least one of an acquisition parameter or a reconstruction parameter based on the image quality index, the pre-determined mapping and the image reader profile.

14. The method of claim 9, further comprising:

receiving an input indicting a change to the image quality index of interest;

updating the at least one of the acquisition parameter or the reconstruction parameter based on the change to the image quality index of interest; and displaying the updated at least one of the acquisition parameter or the reconstruction parameter.

15. The method of claim 14, further comprising:

displaying an estimated dose for the displayed at least one of the acquisition parameter or the reconstruction parameter.

16. The method of claim 15, further comprising:

comparing the estimated dose to a predetermined dose; and displaying a message indicating the estimated dose exceed a predetermined dose threshold in response to the estimated dose exceed a predetermined dose threshold.

17. The method of claim 9, further comprising:

computing a second image quality index based at least on the scan, which provides an image quality index for the actual scan.

* * * * *